United States Patent
Meng et al.

(10) Patent No.: US 11,491,253 B2
(45) Date of Patent: Nov. 8, 2022

(54) AUTOMATIC DRIP FEEDER AND PURIFICATION AND AROMA HUMIDIFIER USING SAME FOR ADDING ESSENTIAL OIL

(71) Applicants: VANSEN INTELLIGENT MANUFACTURING CO., LTD., Fujian (CN); Naturesque LLC, Maple Grove, MN (US)

(72) Inventors: Shifei Meng, Fujian (CN); Xiaowen Zheng, Fujian (CN)

(73) Assignees: VANSEN INIELLIGENT MANUFACTURING CO., LTD., Fujian (CN); NATURESQUE LLC, Maple Grove, MN (US)

( * ) Notice: Subject to any disclaimer, the term of this patent is extended or adjusted under 35 U.S.C. 154(b) by 877 days.

(21) Appl. No.: 16/383,939

(22) Filed: Apr. 15, 2019

(65) Prior Publication Data
US 2020/0306406 A1    Oct. 1, 2020

(30) Foreign Application Priority Data
Mar. 26, 2019  (CN) .......................... 201910233403.3

(51) Int. Cl.
*A61L 9/14* (2006.01)
*A61L 9/013* (2006.01)
*F24F 6/12* (2006.01)

(52) U.S. Cl.
CPC ................. *A61L 9/14* (2013.01); *A61L 9/013* (2013.01); *F24F 6/12* (2013.01); *A61L 2209/11* (2013.01)

(58) Field of Classification Search
None
See application file for complete search history.

(56) References Cited

U.S. PATENT DOCUMENTS

2019/0249888 A1*  8/2019  Chiu .......................... A61L 9/14

FOREIGN PATENT DOCUMENTS

| CN | 203249351 U | 10/2013 |
| CN | 207831563 U | 9/2018 |

* cited by examiner

*Primary Examiner* — Jelitza M Perez
(74) *Attorney, Agent, or Firm* — luncy, Geissler, Olds & Lowe, P.C.

(57) ABSTRACT

The invention discloses an automatic drip feeder and a purification and aroma humidifier using the same for adding essential oil to solve the problem that existing humidifiers have a good aromatic effect in the early stage of usage, while the aromatic effect disappears in the middle and later stages. A water trough of a humidifier body is provided with a receiving groove used for receiving the automatic drip feeder. Essential oil or aromatic liquid is contained in a container of the automatic drip feeder and is quantitatively added into the water trough of the humidifier via a feed port, thus, realizing a continuous purification and aroma effect.

20 Claims, 11 Drawing Sheets

AUTOMATIC DRIP FEEDER AND PURIFICATION AND AROMA HUMIDIFIER USING SAME FOR ADDING ESSENTIAL OIL

BACKGROUND OF THE INVENTION

Technical Field

The invention discloses an automatic drip feeder and a purification and aroma humidifier using the same for adding essential oil, and belongs to the technical field of manufacturing of air purification equipment in terms of International Patent Classification (IPC).

Description of Related Art

Purification and aroma humidifiers are developed by integrating an aroma humidifier and a purification humidifier. At present, there exist, on the market, various aroma humidifiers which have different working principles, such as electric-heating aroma devices and air-blowing aroma devices. Existing humidifiers mainly include ultrasonic humidifiers, water-curtain humidifiers, steam humidifiers and the like.

Chinese Utility Model Patent Literature Publication No. CN203249351U discloses an aroma humidifier which is internally provided with an atomization chamber and an air blower, wherein the atomization chamber is provided with an ultrasonic atomizer, an atomization chamber air inlet and an atomization chamber air outlet. The aroma humidifier is further provided with an essential oil chamber, wherein the essential oil chamber is provided with an essential oil chamber air inlet and an essential oil chamber air outlet, the essential oil chamber air outlet and the atomization chamber air outlet are converged to form a mixed gas outlet. An air flow generated by the air blower is blown into the atomization chamber via the atomization chamber air inlet to blow water mist out via the atomization chamber air outlet, and at the same time, the air flow generated by the air blower is blown into the essential oil chamber via the essential oil chamber air inlet to blow volatilized essential oil out via the essential oil chamber air outlet; and the water mist and the volatilized essential oil are mixed in the mixed gas outlet to form a mixed gas, and therefore, an aromatic humidification effect is realized.

Most aroma humidifiers on the market work based on the combination of the two ways mentioned above, and the way of atomizing aromatic substances after the aromatic substances are added to water gains the highest acceptance from the market. The aromatic substances are added to water and are then ultrasonically atomized to be diffused in the environment, and indoor air is improved by negative ions, humidity and fragrances generated by ultrasonic atomization to create a comfortable and healthy home environment. After aromatic substances such as essential oil and perfumes are added to water, essential oil molecules and water molecules are decomposed into ultrafine micro-particles by ultrasonic vibration, and negative ions are generated at the same time; and then, atomized essential oil is blown out by a fan together with water mist and the negative ions. Every time the purification and aroma humidifiers on the existing market are used, essential oil and perfumes have to be manually added. In order to fulfill the humidification effect, the aroma humidifiers should have a higher water capacity and a higher humidification capacity than aroma diffusers; and due to the fact that most aromatic mist (such as pure natural essential oil) is insoluble and cannot be dissolved in water, a good aromatic effect can be achieved in the early state, while this aromatic effect may disappear in the middle and later stages.

Chinese Utility Model Patent Literature Publication No. CN207831563U discloses a humidifier capable of regularly and quantitatively adding essential oil. This humidifier is provided with a humidifier body, a water barrel assembled on the humidifier body and an essential oil feeder assembled on the humidifier body, wherein the essential oil feeder comprises a shell, at least one essential oil bottle arranged in the shell and having one type of essential oil stored therein, and at least one peristaltic pump corresponding to the essential oil bottle and used for conducting control after being connected to the humidifier body. In this solution, the peristaltic pumps are used for feeding essential oil.

BRIEF SUMMARY OF THE INVENTION

To overcome the defects of manual addition of existing purification and aroma humidifiers, the invention provides an automatic drip feeder capable of continuously and controllably adding essential oil, aromatic liquid or any other desired liquid.

Meanwhile, the invention further provides a purification and aroma humidifier using the automatic drip feeder for adding essential oil. Essential oil is continuously added to the humidifier, so that the problem of the lack of an aromatic effect in the middle and later stages of existing aroma humidifiers is solved.

To fulfill the above objective, the following technical solution is adopted by the invention:

An automatic drip feeder comprises at least one container, at least one container cover matched with the container, and at least one piston air pump, wherein:

The container is used for containing to-be-added liquid, the container cover is matched with the container and is provided with an air inlet and an outlet, and the outlet is connected with a hollow tube and extends into the container;

The piston air pump is provided with a suction port and an air outlet, the air outlet is communicated with the air inlet of the container, and a piston of the piston air pump is driven by a driving part to reciprocate to realize air suction or exhaust; when the piston air pump exhausts air, the air is guided into the container, so that the liquid in the container drops out via the outlet; every time the piston is driven by the driving part to reciprocate once, a touch switch is synchronously triggered, so that the reciprocating times of the piston are obtained, and then the liquid is controllably added;

One air pump corresponds to one container, or one piston air pump corresponds to two or more containers.

Furthermore, the driving part is a motor connected with a combined cam, wherein the combined cam comprises a piston action part and a switch action part, the piston action part is an eccentric wheel used for driving the piston to move forwards or backwards, the switch action part is a rotating wheel having an annular face and a flat face, and the eccentric wheel and the rotating wheel form a combined wheel body capable of synchronously rotating; and in the rotating process, when the annular face rotates to the touch switch, the touch switch is pressed by the annular face; when the flat face rotates to the touch switch, the touch switch is turned off; signals are transmitted to a control center according to the on-off state of the touch switch, and the quantity of air generated by the piston air pump is calculated according to signal triggering times, so that liquid is quantitatively added.

Furthermore, the motor and the piston air pump are arranged on a fixed frame, the piston of the piston air pump is connected with a piston rod, the piston rod penetrates through a corresponding hole of the fixed frame to interact with the piston action part of the combined cam, and the piston and the piston rod always abut against a circumferential surface of the piston action part under the effects of a spring so as to realize reciprocating motions.

Furthermore, the piston air pump comprises a cylinder body, a membrane and a valve deck, an end face of the cylinder body is assembled on the valve deck through the membrane and is provided with an exhaust hole and a suction hole, the valve deck is provided with an air exhaust channel and an air suction channel which respectively correspond to the exhaust hole and the suction hole in the end face of the cylinder body, the membrane is provided with an air exhaust part and an air suction part, the air exhaust part corresponds to the air exhaust channel and the exhaust hole, and the air suction part corresponds to the air suction channel and the suction hole, wherein:

an opening of the exhaust channel of the valve deck is larger than the air exhaust part of the membrane, and the air exhaust part of the membrane is larger than the exhaust hole in the end face of the cylinder body;

an opening of the air suction channel of the valve deck is smaller than the air suction part of the membrane, and the air suction part of the membrane is smaller than the suction hole in the end face of the cylinder body.

Furthermore, the driving part is an electromagnet, and the piston of the piston air pump reciprocates under the cooperative effect of an elastic piece and the electromagnet.

Furthermore, the container cover comprises an outer cover and an inner cover, the air inlet and the outlet are formed in the outer cover and penetrate through the inner cover to extend into an inner cavity of the container, the inner cover is connected with the container in a threaded manner, an annular clamping groove is formed in the inner cover in a circumferential direction, the outer cover is installed and positioned in the clamping groove through one or more fasteners arranged on a side face of the outer cover, and a matching face of the outer cover and the inner cover is provided with an axial positioning column and an axial matching groove to define the direction of the air inlet and the direction of the outlet.

A purification and aroma humidifier comprises the automatic drip feeder and a humidifier body, wherein a water trough of the humidifier body is provided with a receiving groove used for receiving the automatic drip feeder, and essential oil or aromatic liquid is contained in the container of the automatic drip feeder and is quantitatively added into the water trough of the humidifier via a feed port.

Furthermore, the automatic drip feeder adopts at least one of the following modes to add the aromatic liquid:

(1) to add the aromatic liquid via a preset control mode of the purification and aroma humidifier;

(2) to add the aromatic liquid via a manual addition mode on a control panel;

(3) to control the addition of the aromatic liquid via mobile phone APP software.

Furthermore, an atomization module is arranged at the bottom of the water trough of the humidifier body and is used for atomizing water containing the essential oil in the water trough to generate negative ions, the atomized essential oil is blown out by a fan together with water mist and the negative ions, the fan is arranged at the bottom of the water trough and is provided with an air port located above the liquid level in the water trough, a water level detector is arranged in the water trough, and the water trough supplies water in cooperation with a water tank.

Furthermore, a bottom cover is arranged at the bottom of the water trough and is provided with a control circuit, the water tank is arranged in the water trough, a drain hole is formed in the bottom of the water tank, a drain control device is arranged at the drain hole, an atomization tube is arranged in the water tank, and a top cover is arranged at the top of the water tank and is provided with a mist outlet matched with the atomization tube.

As an independent module, the automatic drip feeder can be applied to various humidifiers, aroma diffusers and aroma humidifiers to automatically add essential oil, can also be applied to perfume blenders and essential oil compound machines having a requirement for automatic liquid addition, and can automatically add aromatic substances as well as any liquids. The purification and aroma humidifier using the automatic drip feeder solves the problem that most existing humidifiers have a good aromatic effect in the early stage in use, while the aromatic effect disappears in the middle and later stages.

DETAILED DESCRIPTION OF THE INVENTION

Figure 1:
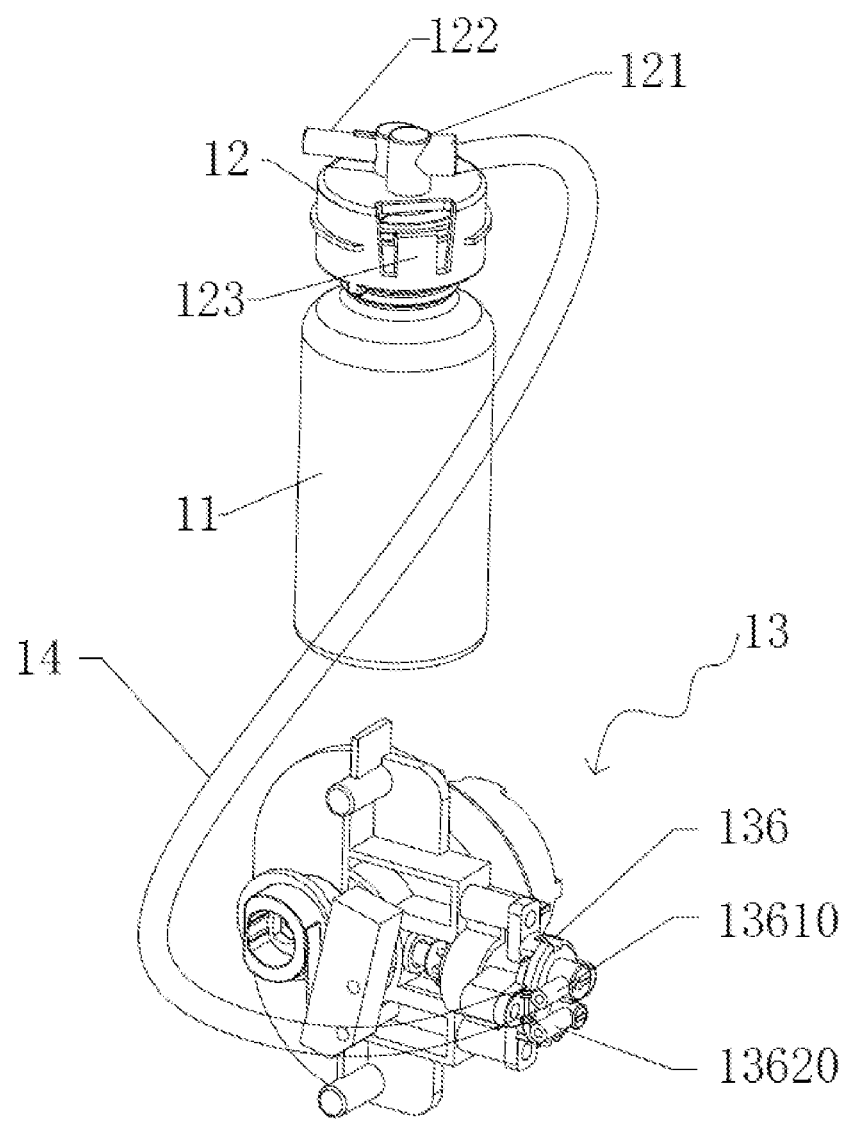
FIG. 1 is a schematic diagram of an automatic drip feeder of the invention.
Figure 2:
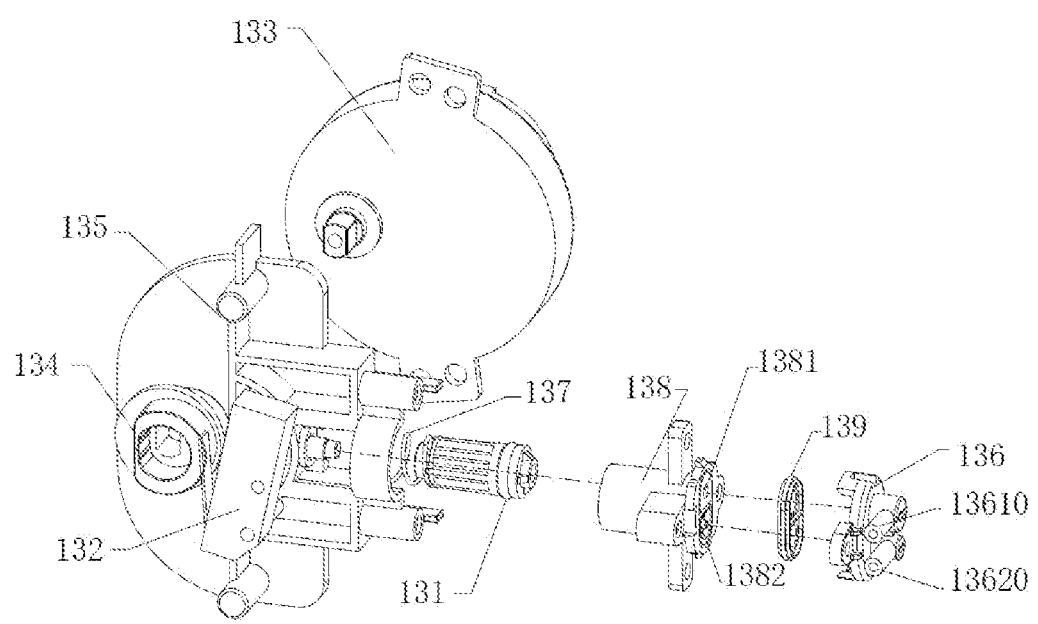
FIG. 2 is an exploded view of a piston air pump of the invention.

The invention is further described below in combination with the accompanying drawings.

Embodiment: Referring to FIGS. 1-8, an automatic drip feeder 1 comprises at least one container 11, at least one container cover 12 matched with the container 11, and at least one piston air pump 13. The container 11 is used for containing to-be-added liquid, such as aromatic liquid W. The container cover 12 is matched with the container 11 and is provided with an air inlet 121 and an outlet 122, wherein the outlet 122 is connected with a hollow tube 123 and extends into the container. The piston air pump 13 is provided with a suction port 13620 and an air outlet 13610, wherein the air outlet is communicated with the air inlet of the container via a hose 14 or an air tube. A piston 131 of the piston air pump 13 is controlled by a driving part to reciprocate to realize air suction or exhaust. When the piston air pump 13 exhausts air, air is guided into the container 11, so that the liquid in the container drops out via the outlet 122. Every time the piston 131 is driven by the driving part to reciprocate once, a touch switch 132 is synchronously triggered, so that the reciprocating times of the piston 131 are obtained, and accordingly, liquid is controllably added. One piston air pump corresponds to one container, or one piston air pump corresponds to two or more containers. Substances that can be automatically added by the automatic drip feeder 1 include, but are not limited to, aromatic substances such as essential oil, and can also be any liquids. A motor 133 can be used as the driving part of the automatic drip feeder 1. The motor 133 is connected with a combined cam 134 comprising a piston action part 1341 and a switch action part 1342, wherein the piston action part 1341 is an eccentric wheel capable of driving the piston to move forwards or backwards; when the eccentric wheel is located on a short side, the piston retreats under the effect of a spring, and when the eccentric wheel rotates to a long side, the piston is pushed forwards, so that reciprocating motions of the piston are realized; the switch action part 1342 is a rotating wheel has an annular face and a flat face, and a combined wheel body capable of synchronously rotating is formed by the eccentric wheel and the rotating wheel; in the rotating process, when the annular face rotates to the touch switch, the touch switch is pressed by the annular face; when the flat face rotates to the touch switch, the touch switch is turned off; signals are transmitted to a control center or a control circuit according to the on-off state of the touch switch, the quantity of air generated by the piston air pump is calculated according to signal triggering times, and then liquid is quantitatively added. The motor 133 and the piston air pump 13 are arranged on a fixed frame 135. The piston 131 of the piston air pump is connected with a piston rod which penetrates through a corresponding hole of the fixed frame 135 to interact with the piston action part of the combined cam 134, and the piston and the piston rod always abut against the circumferential surface of the piston action part under the effect of a spring 137 so as to realize reciprocating motions. The piston air pump 13 comprises a cylinder body 138, a membrane 139 and a valve deck 136. An end face of the cylinder body 138 is assembled on the valve deck 136 via the membrane 139 and is provided with an exhaust hole 1381 and a suction hole 1382. The valve deck 136 is provided with an air exhaust channel and an air suction channel which respectively correspond to the exhaust hole and the suction hole in the end face of the cylinder body 138. The membrane 139 is provided with an air exhaust part 1391 and an air suction part 1392, wherein the air exhaust part 1391 corresponds to the air exhaust channel 1361 and the exhaust hole, and the air suction part 1392 corresponds to the air suction channel 1362 and the suction hole. The matching relationship of the membrane, the end face of the cylinder body and the valve deck is as follows:

An opening of the air exhaust channel of the valve deck is larger than the air exhaust part of the membrane, and the air exhaust part of the membrane is larger than the exhaust hole in the end face of the cylinder body;

An opening of the air suction channel of the valve deck is smaller than the air suction part of the membrane, and the air suction part of the membrane is smaller than the suction hole in the end face of the cylinder body;

The suction hole is porous, and an ejection core is disposed at the suction hole to interact with the air suction part of the membrane. An ejection column 1363 is arranged in the air exhaust channel of the valve deck and is matched with the air exhaust part of the membrane. The membrane is partitioned from the middle by a partition into an air suction area and an air exhaust area. The air suction area and the air exhaust area each comprise an intermediate membrane and peripheral fixing parts spaced from one another, wherein the fixing parts and the intermediate membrane are connected through a connecting part, and an annular non-closed through-hole structure is formed between the fixing part and the intermediate membrane.

Besides the motor, an electromagnet can also be used for driving the automatic drip feeder 1. In this case, the piston of the piston air pump reciprocates under the cooperative effect of an elastic piece and the electromagnet, wherein the elastic piece is a spring or other elastic pieces matched with the piston.

Figure 3:
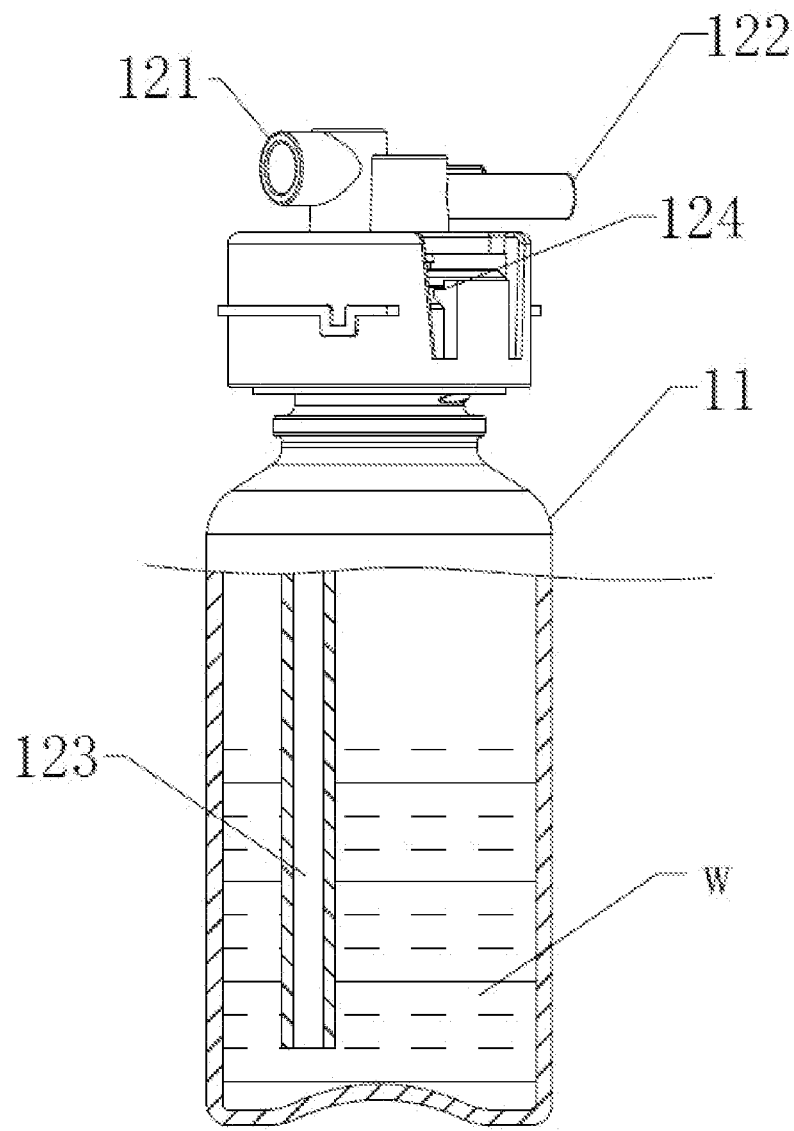
FIG. 3 is a schematic diagram of a liquid container of the invention.
Figure 4:
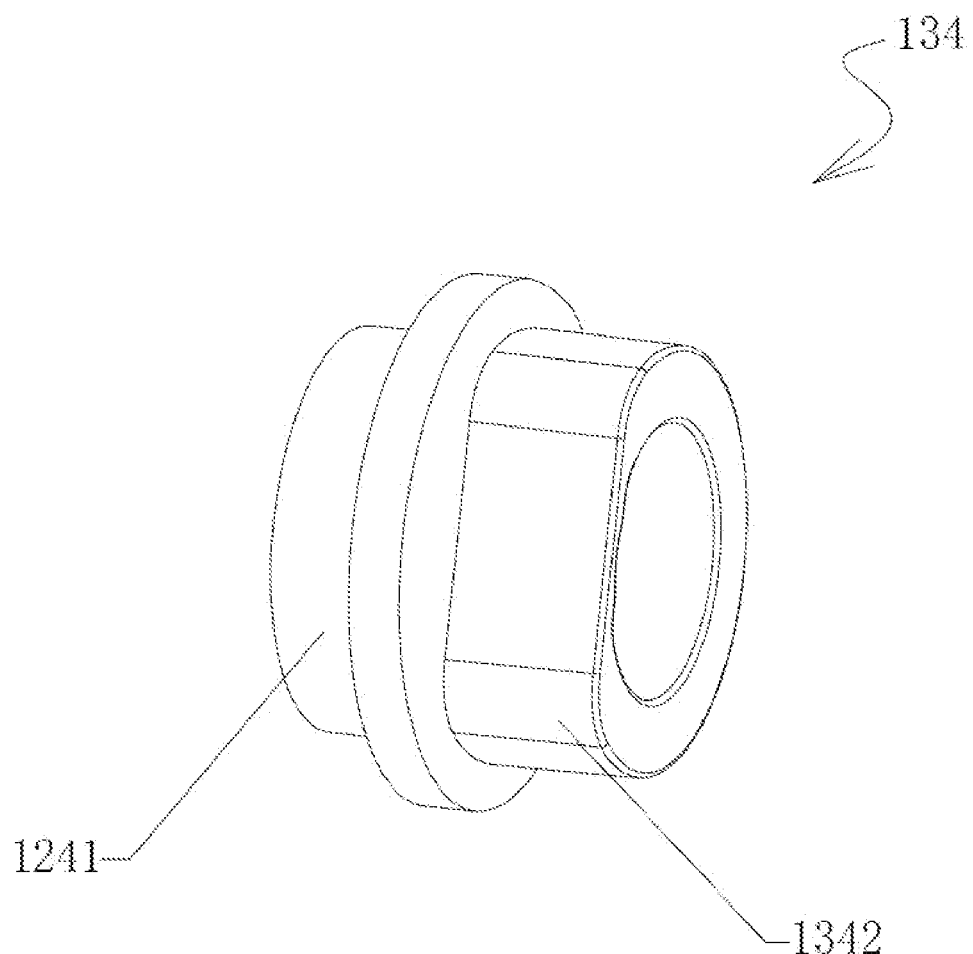
FIG. 4 is a schematic diagram of a combined cam of the invention.
Figure 5:
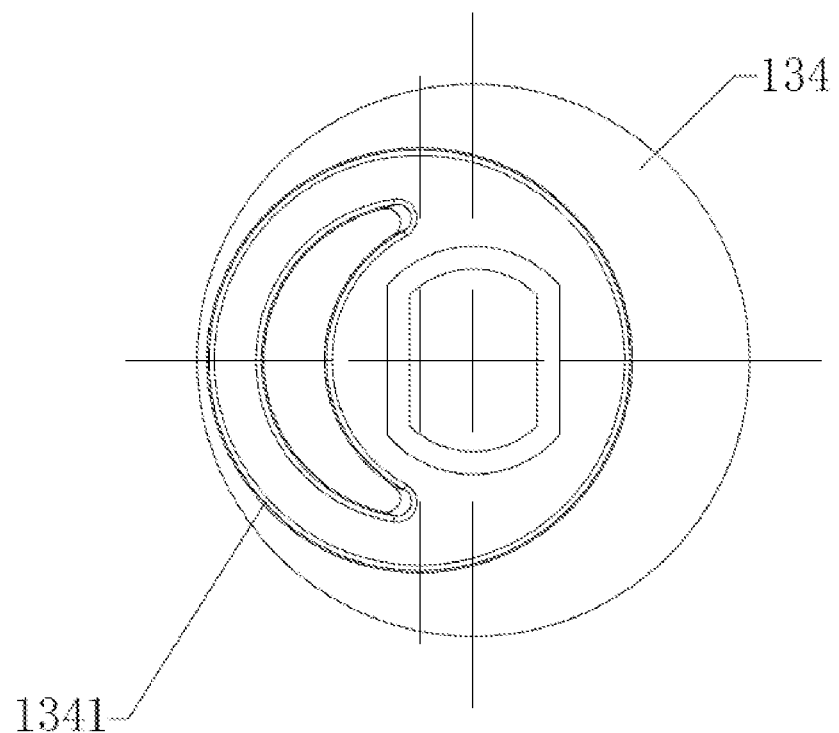
FIG. 5 is a schematic diagram of a piston action part of the combined cam.
Figure 6:
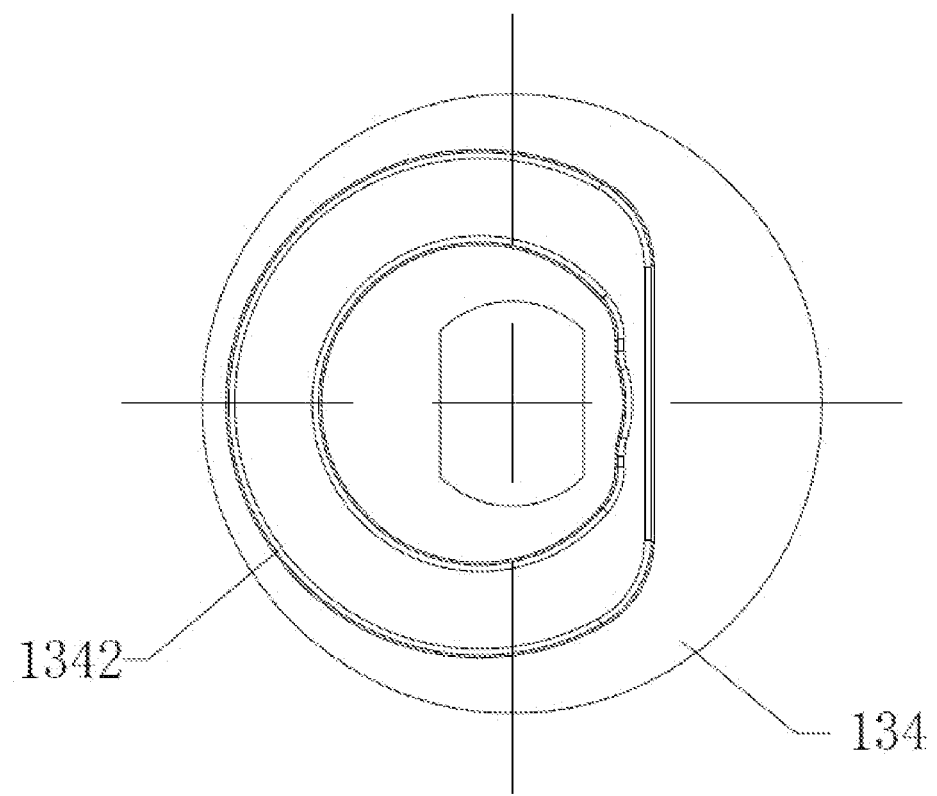
FIG. 6 is a schematic diagram of a switch action part of the combined cam.
Figure 7:
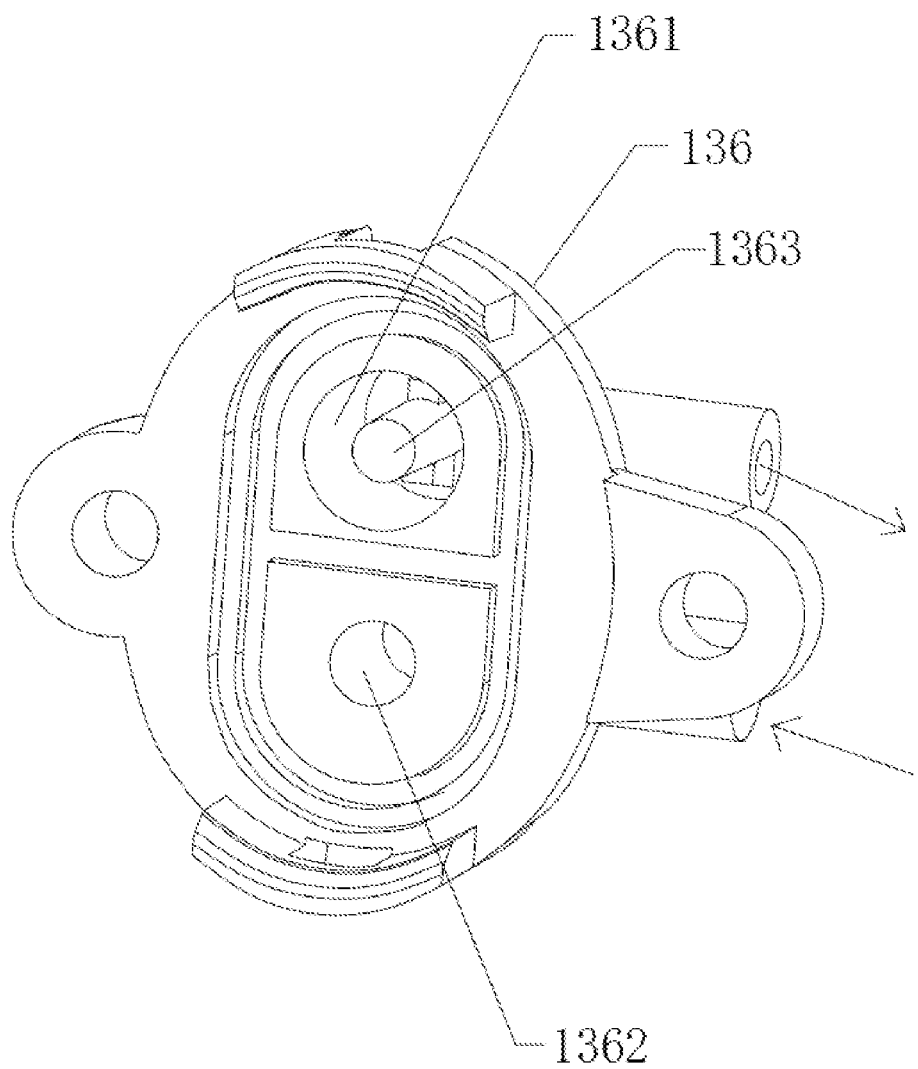
FIG. 7 is schematic diagram of a valve deck.
Figure 8:
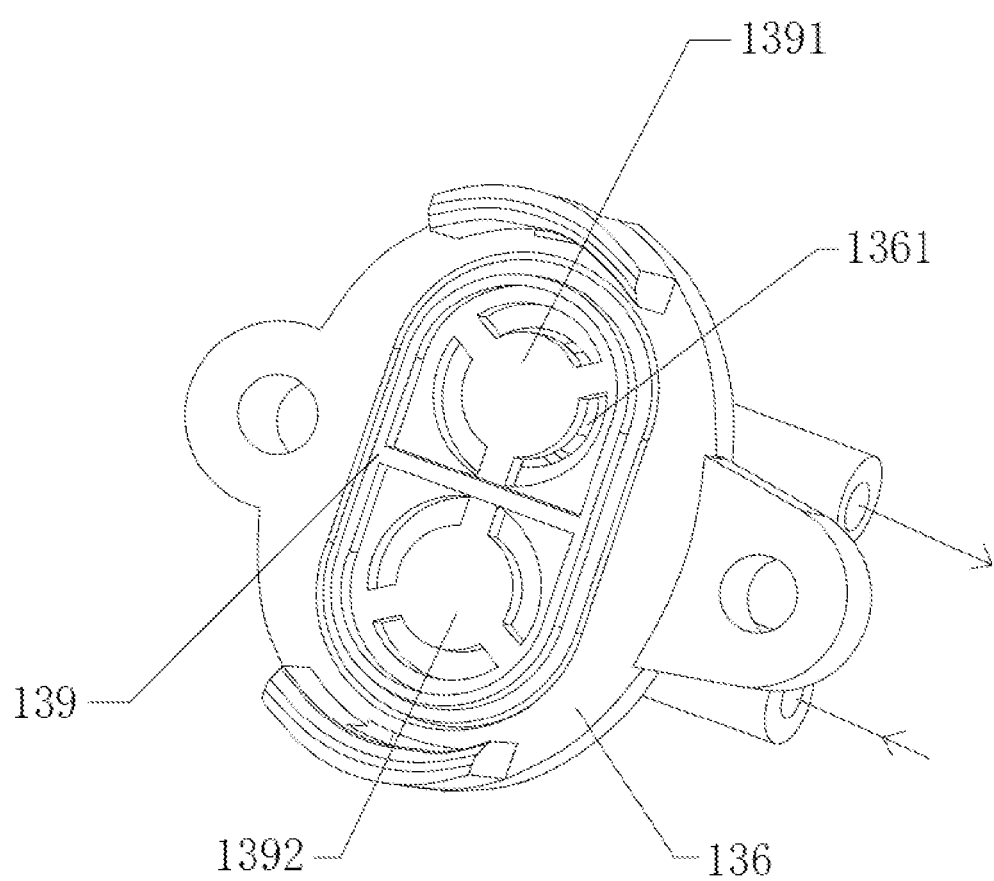
FIG. 8 is a schematic diagram of the cooperation between the valve deck and a membrane.

As shown in FIG. 1 or FIG. 3, the container cover of the automatic drip feeder 1 comprises an outer cover and an inner cover, wherein the air inlet and the outlet are formed in the outer cover and penetrate through the inner cover to extend into an inner cavity of the container, the inner cover is connected with the container in a threaded manner, an annular clamping groove is formed in the inner cover in a circumferential direction, the outer cover is installed and positioned in the clamping groove through one or more fasteners 124 arranged on a side face of the outer cover, a matching surface of the outer cover and the inner cover is provided with an axial positioning column and an axial matching groove which are used to define the direction of the air inlet and the direction of the outlet, a periphery of the outer cover is provided with a connecting part and is installed at an installation position in a matched manner, and the installation position is located on a corresponding humidifier or other devices; or, the container cover is directly integrated on an installation device of the corresponding humidifier, and the container is directly connected to a corresponding position.

The technical issue to be settled by the invention is to provide a device capable of automatically adding liquid aromatic substances, namely the automatic drip feeder. The automatic drip feeder can automatically add essential oil in work through mode setting, can control the addition of the essential oil through a key and can also add different types of aromatic substances or add the aromatic substances in different promotions by designing multiple adding devices.

Figure 9:
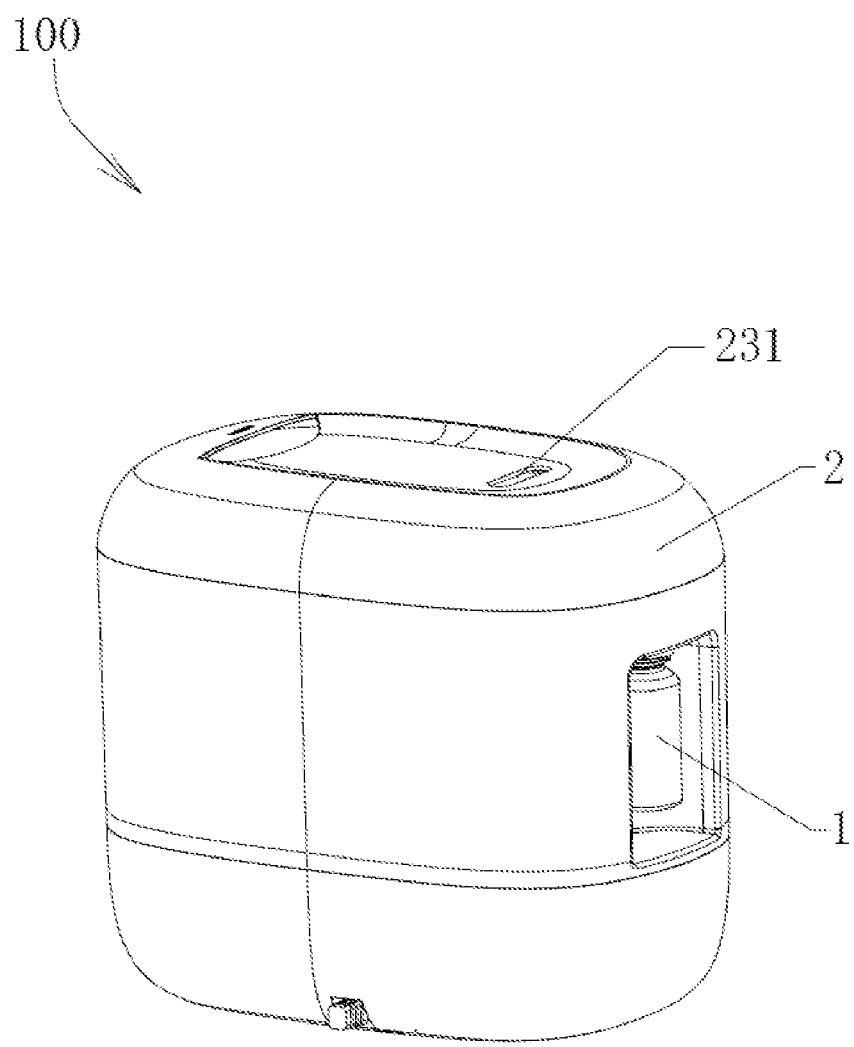
FIG. 9 is an overall schematic diagram of a purification and aroma humidifier.
Figure 10:
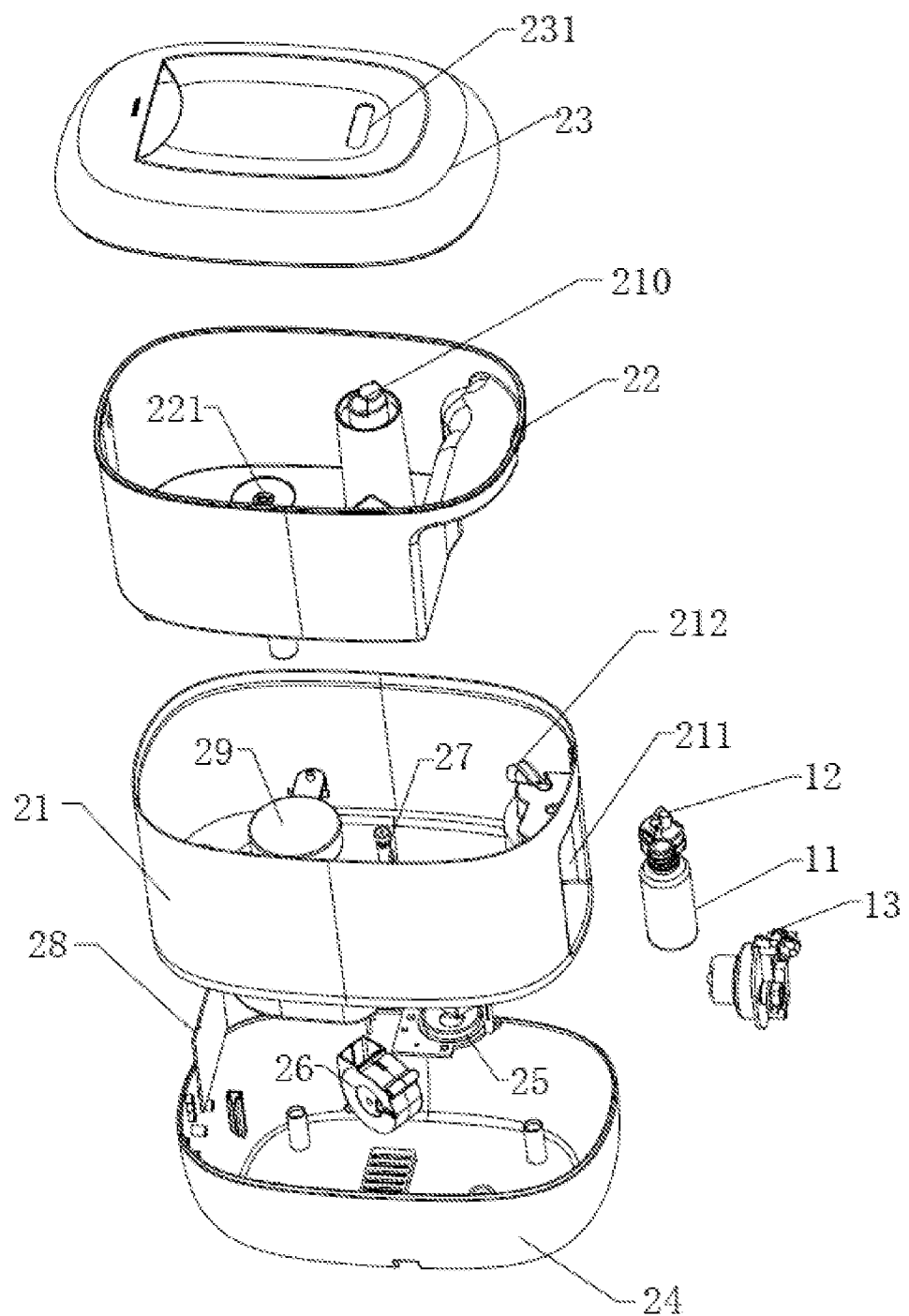
FIG. 10 is an exploded view of FIG. 9.
Figure 11:
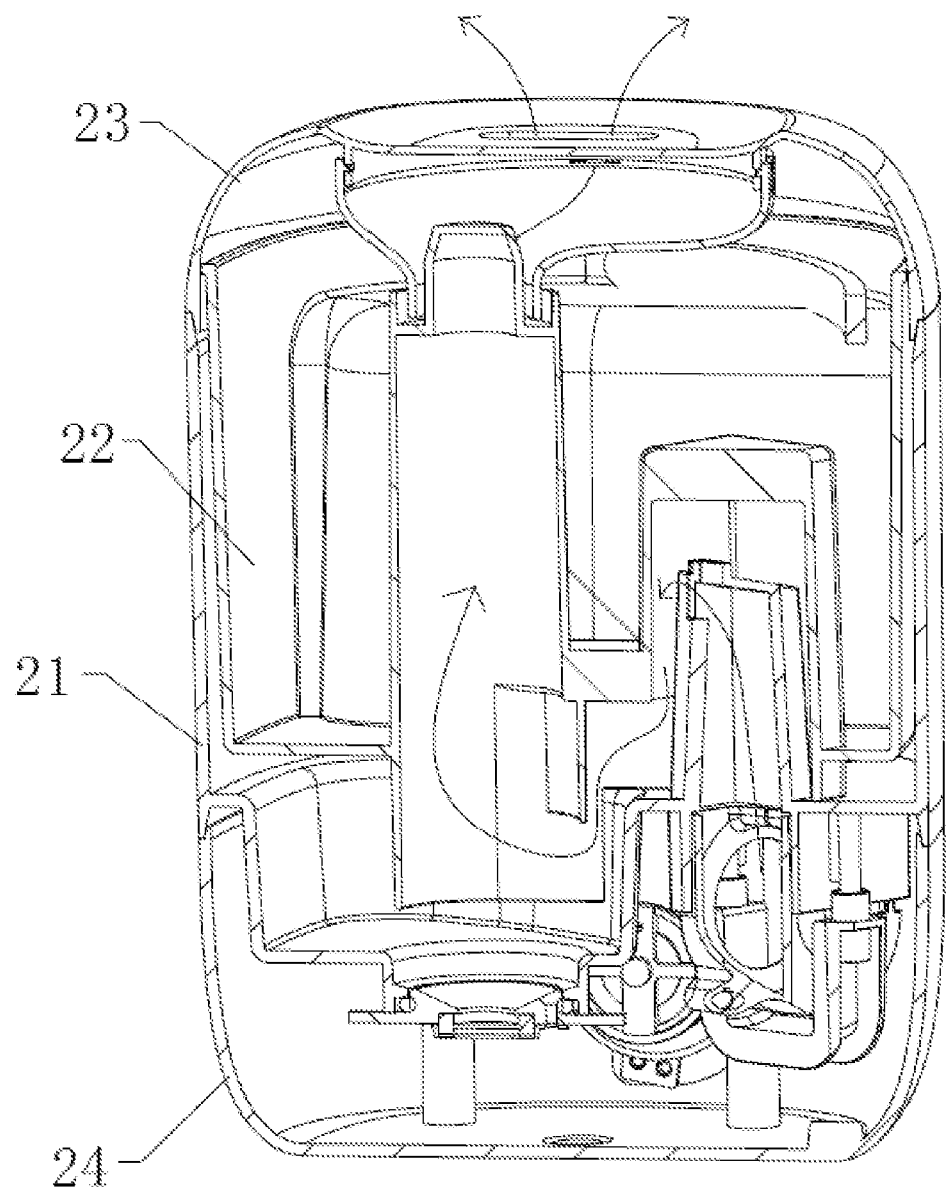
FIG. 11 is a sectional view of FIG. 9.

As shown in FIGS. 9-11, a purification and aroma humidifier 100 comprises the automatic drip feeder 1 and a humidifier body 2. A water trough 21 of the humidifier body 2 is provided with a receiving groove 211 used for receiving the automatic drip feeder 1. Essential oil or aromatic liquid is contained in the container of the automatic drip feeder and can be quantitatively added into the water trough 21 of the humidifier via a feed port 212. The automatic drip feeder 1 adopts at least one of the following modes to add the aromatic liquid:

(1) add the aromatic liquid via a preset control mode of the purification and aroma humidifier;

(2) add the aromatic liquid via a manual addition mode on a control panel;

(3) control the addition of the aromatic liquid via mobile phone APP software, for instance, adding the aromatic liquid in use of the humidifier.

As shown in FIG. 10, an atomization module 25 is arranged at the bottom of the water trough 21 of the humidifier body 2 and is used for atomizing water containing essential oil in the water trough to generate negative ions, and then the atomized essential oil is blown out by a fan 26 together with water mist and the negative ions. The fan 26 is arranged at the bottom of the water trough 21 and is provided with an air port located above the liquid level in the water trough. A water level detector 27 is arranged in the water trough 21. The water trough 21 supplies water in cooperation with a water tank 22. A bottom cover 24 is arranged at the bottom of the water trough 21 and is provided with a control circuit 28. The water tank 22 is arranged in the water trough 21. A drain hole 221 is formed in the bottom of the water tank 22. The water trough is provided with a drain control device 29 corresponding to the drain hole. An atomization tube 210 is arranged in the water tank 22. A top cover 23 is arranged at the top of the water tank 22 and is provided with a mist outlet 231 matched with the atomization tube.

In FIG. 11, an air flow generated by a fan or an air blower is exhausted via an atomization port in the arrow direction.

The invention solves the problem that most existing aroma humidifiers have a good aromatic effect in the early stage, while the aromatic effect disappears in the middle and later stages. According to the technical solution, the purification and aroma humidifier capable of automatically and quantitatively adding essential oil comprises a top cover, a water tank, a water trough, a bottom cover, an atomization module, a control circuit, an air blower, a bottle cap, a bottle, an air pump module and the like, wherein the top cover is provided with a mist outlet, and the water tank is provided with an atomization tube and a drain hole; a drain control device, a water level detection device, a feed port, a storage groove, an atomization module, the air blower and the air pump module are installed on the water trough; the control circuit is fixed to the bottom cover and then is locked on the water trough; the water tank is arranged in the water trough and is covered with the top cover, and the bottle is placed in the storage groove in the water trough after the bottle cap is assembled on the bottle.

The operating principle of the solution adopted by the invention is as follows:

When water in the water tank 22 reaches the highest water level, the water tank 22 is placed in the water trough 21 and is covered with the top cover 23. The atomization switch is turned on, then the drain control device 29 in the water trough 21 is started, and water in the water tank enters the water trough 21 via the drain hole 221; and when water in the water trough reaches the optimal position, the drain hole is controlled by the drain control device 29 to close. When the water level detection device (the water level detector 27) in the water trough 21 detects that water exists in the water trough, the ultrasonic atomization module and the fan 26 are started, ultrasonically-generated mist is diffused into the environment by the fan, and a purification humidification mode is started. When an aroma mode is stated, the air pump module starts to work to generate air, which is in turn injected into the bottle via a hose connected between the air pump and the bottle cap; after air enters the bottle, aromatic liquid is compressed by the air to drop into the water trough via the feed port 212 in the water trough 21; and finally, the aromatic liquid is diffused into the environment through the ultrasonic atomization module and the fan together with water in the water trough. The quantity of addition and the interval of addition can be set via a preset control mode. In addition, aromatic liquid can be added in use of the humidifier via a manual addition module on a control panel, an APP or the like.

When the essential oil adding mode is started, the control circuit 28 outputs a signal to control the motor 133 to rotate, the motor drives the cam to operate, and the piston is driven by the cam to reciprocate in the cylinder; when the piston retreats, air enters the cylinder via the suction port after passing though the membrane, and in the air suction process, the membrane blocks the rear end of the air outlet, namely the air exhaust part of the membrane seals the exhaust hole in the end face of the cylinder body, so that air is prevented from entering the air outlet; when the piston advances, air in the cylinder is squeezed out and is exhausted via the air outlet after passing through the membrane, and in the exhaust process, the membrane blocks the suction port, namely the air suction part of the membrane seals the matching opening of the air suction channel of the valve, so that air is prevented from being exhausted via the suction port. Springs are arranged on the piston and the cylinder and are used for driving the piston to retreat, and a seal ring is arranged on the piston to prevent air from being exhausted out of the cylinder. Air exhausted via the air outlet enters the bottle via the air inlet connected between the air outlet and the bottle cap, and the bottle is sealed by the bottle cap. When a certain quantity of air is injected into the bottle, and aromatic liquid in the bottle is correspondingly squeezed out by the air injected into the bottle, is discharged out of the hollow tube via the exhaust port, and finally drops into water through via the feed port in the water trough. The touch switch is additionally arranged on the fixed frame and is triggered once by the cam every time the cam rotates to the touch switch, and signals are transmitted to the control circuit at the same time; and when the cam rotates for set times, the motor is controlled through the control panel to stop; and the quantity of air is obtained by multiplying the rotating times of the cam (namely the reciprocating times of the piston) by the volume of air generated every time, and thus, the aromatic liquid is quantitatively added.

What should be pointed out about the invention is as follows:

1. The air pump device matched with the aromatic liquid storage container is not limited to the quantitative piston air pump mentioned above and can also be a simple air pump motor; the piston air pump works through, but not limited to, the combination of the cam and the spring mentioned above and can also work through the combination of the cam and other elastic pieces, or through a cam-connecting rod mechanism which is able to drive the piston to reciprocate through a cam and a connecting rod; and the piston air pump is driven by, but not limited to, the motor and can also be driven by the combination of an electromagnet and an elastic piece or the combination of attraction of the electromagnet and an elastic force of the elastic piece.

2. The structure of the automatic drip feeder and the purification and aroma humidifier is not limited to one aroma liquid container (bottle), and it is also applicable that one air pump corresponds to multiple aroma liquid containers (bottles) or multiple air pumps corresponds to multiple aroma liquid containers (bottles).

3. The automatic drip feeder can serve as an independent module to be applied, to various humidifiers, aroma diffusers and aroma humidifiers instead of a certain type of purification humidifiers; the automatic drip feeder can also be applied to perfume blenders, essential oil compound machines and other products having a requirement for automatic liquid addition, besides the humidifiers and the aroma diffusers; and the automatic drip feeder can automatically add aromatic substances as well as any liquids.

4. The drain control mode of the purification and aroma humidifier is not limited to the one mentioned above, and both a mechanical drain control mode and an electronic drain control mode can be adopted, such as a water cap, a floater, an electromagnetic valve and an electromagnet adopted by traditional humidifiers; the overall structures of the products mentioned above are not limited to the ones shown in the drawings, for instance, the water tank is an airtight water tank, or the water tank is an open water tank; the water tank is placed in the water trough, or the water tank is placed above the water trough; the water tank can be adopted, or no water tank is adopted, and a big water trough is used for containing water.

The above embodiments are only illustrative ones of the technical contents of the invention. All modifications or variations made by any skilled in this field based on the principle of the invention should also fall within the patent scope of the invention. The invention is not limited to the illustrative ones disclosed above.

What is claimed is:

1. An automatic drip feeder, comprising at least one container, at least one container cover matched with the container, and at least one piston air pump, wherein:
    the container is used for containing to-be-added liquid, the container cover is matched with the container and is provided with an air inlet and an outlet, and the outlet is connected with a hollow tube and extends into the container;
    the piston air pump is provided with a suction port and an air outlet, the air outlet is communicated with the air inlet of the container, and a piston of the piston air pump is driven by a driving part to reciprocate to realize air suction or exhaust; when the piston air pump exhausts air, the air is guided into the container, so that the liquid in the container drops out via the outlet; every time the piston is driven by the driving part to reciprocate once, a touch switch is synchronously triggered, so that the reciprocating times of the piston are obtained, and then the liquid is controllably added;
    one said piston air pump corresponds to one said container, or one said piston air pump corresponds to two or more said containers.

2. The automatic drip feeder according to claim 1, wherein the driving part is a motor connected with a combined cam, the combined cam comprises a piston action part and a switch action part, the piston action part is an eccentric wheel used for driving the piston to move forwards or backwards, the switch action part is a rotating wheel having an annular face and a flat face, and the eccentric wheel and the rotating wheel form a combined wheel body capable of synchronously rotating; and in the rotating process, when the annular face rotates to the touch switch, the touch switch is pressed by the annular face; when the flat face rotates to the touch switch, the touch switch is turned off; signals are transmitted to a control center according to the on-off state of the touch switch, and the quantity of air generated by the piston air pump is calculated according to signal triggering times, so that liquid is quantitatively added.

3. The automatic drip feeder according to claim 2, wherein the motor and the piston air pump are arranged on a fixed frame, the piston of the piston air pump is connected with a piston rod, the piston rod penetrates through a corresponding hole of the fixed frame to interact with the piston action part of the combined cam, and the piston and the piston rod always abut against a circumferential surface of the piston action part under the effects of a spring so as to realize reciprocating motions.

4. The automatic drip feeder according to claim 1, wherein the piston air pump comprises a cylinder body, a membrane and a valve deck, an end face of the cylinder body is assembled on the valve deck through the membrane and is provided with an exhaust hole and a suction hole, the valve deck is provided with an air exhaust channel and an air suction channel which respectively correspond to the exhaust hole and the suction hole in the end face of the cylinder body, the membrane is provided with an air exhaust part and an air suction part, the air exhaust part corresponds to the air exhaust channel and the exhaust hole, and the air suction part corresponds to the air suction channel and the suction hole, wherein:
    an opening of the air exhaust channel of the valve deck is larger than the air exhaust part of the membrane, and the air exhaust part of the membrane is larger than the exhaust hole in the end face of the cylinder body;
    an opening of the air suction channel of the valve deck is smaller than the air suction part of the membrane, and the air suction part of the membrane is smaller than the suction hole in the end face of the cylinder body.

5. The automatic drip feeder according to claim 1, wherein the driving part is an electromagnet, and the piston of the piston air pump reciprocates under the cooperative effect of an elastic piece and the electromagnet.

6. The automatic drip feeder according to claim 1, wherein the container cover comprises an outer cover and an inner cover, the air inlet and the outlet are formed in the outer cover and penetrate through the inner cover to extend into an inner cavity of the container, the inner cover is connected with the container in a threaded manner, an annular clamping groove is formed in the inner cover in a circumferential direction, the outer cover is installed and positioned in the annular clamping groove through one or more fasteners arranged on a side face of the outer cover, and a matching face of the outer cover and the inner cover is provided with an axial positioning column and an axial matching groove to define a direction of the air inlet and a direction of the outlet.

7. A purification and aroma humidifier, comprising the automatic drip feeder according to claim 1 and a humidifier body, wherein a water trough of the humidifier body is provided with a receiving groove used for receiving the automatic drip feeder, and essential oil or aromatic liquid is contained in the container of the automatic drip feeder and is quantitatively added into the water trough of the humidifier via a feed port.

8. A purification and aroma humidifier, comprising the automatic drip feeder according to claim 2 and a humidifier body, wherein a water trough of the humidifier body is provided with a receiving groove used for receiving the automatic drip feeder, and essential oil or aromatic liquid is contained in the container of the automatic drip feeder and is quantitatively added into the water trough of the humidifier via a feed port.

9. A purification and aroma humidifier, comprising the automatic drip feeder according to claim 3 and a humidifier body, wherein a water trough of the humidifier body is provided with a receiving groove used for receiving the automatic drip feeder, and essential oil or aromatic liquid is contained in the container of the automatic drip feeder and is quantitatively added into the water trough of the humidifier via a feed port.

10. A purification and aroma humidifier, comprising the automatic drip feeder according to claim 4 and a humidifier body, wherein a water trough of the humidifier body is provided with a receiving groove used for receiving the automatic drip feeder, and essential oil or aromatic liquid is contained in the container of the automatic drip feeder and is quantitatively added into the water trough of the humidifier via a feed port.

11. A purification and aroma humidifier, comprising the automatic drip feeder according to claim 6 and a humidifier body, wherein a water trough of the humidifier body is provided with a receiving groove used for receiving the automatic drip feeder, and essential oil or aromatic liquid is contained in the container of the automatic drip feeder and is quantitatively added into the water trough of the humidifier via a feed port.

12. The purification and aroma humidifier according to claim 7, wherein an atomization module is arranged at a bottom of the water trough of the humidifier body and is used for atomizing water containing the essential oil in the water trough to generate negative ions, the atomized essential oil is blown out by a fan together with water mist and the negative ions, the fan is arranged at the bottom of the water trough and is provided with an air port located above a liquid level in the water trough, a water level detector is arranged in the water trough, and the water trough supplies water in cooperation with a water tank.

13. The purification and aroma humidifier according to claim 8, wherein an atomization module is arranged at a bottom of the water trough of the humidifier body and is used for atomizing water containing the essential oil in the water trough to generate negative ions, the atomized essential oil is blown out by a fan together with water mist and the negative ions, the fan is arranged at the bottom of the water trough and is provided with an air port located above a liquid level in the water trough, a water level detector is arranged in the water trough, and the water trough supplies water in cooperation with a water tank.

14. The purification and aroma humidifier according to claim 10, wherein an atomization module is arranged at a bottom of the water trough of the humidifier body and is used for atomizing water containing the essential oil in the water trough to generate negative ions, the atomized essential oil is blown out by a fan together with water mist and the negative ions, the fan is arranged at the bottom of the water trough and is provided with an air port located above a liquid level in the water trough, a water level detector is arranged in the water trough, and the water trough supplies water in cooperation with a water tank.

15. The purification and aroma humidifier according to claim 12, wherein a bottom cover is arranged at the bottom of the water trough and is provided with a control circuit, the water tank is arranged in the water trough, a drain hole is formed in a bottom of the water tank, a drain control device is arranged at the drain hole, an atomization tube is arranged in the water tank, and a top cover is arranged at a top of the water tank and is provided with a mist outlet matched with the atomization tube.

16. The purification and aroma humidifier according to claim 13, wherein a bottom cover is arranged at the bottom of the water trough and is provided with a control circuit, the water tank is arranged in the water trough, a drain hole is formed in a bottom of the water tank, a drain control device is arranged at the drain hole, an atomization tube is arranged in the water tank, and a top cover is arranged at a top of the water tank and is provided with a mist outlet matched with the atomization tube.

17. The purification and aroma humidifier according to claim 14, wherein a bottom cover is arranged at the bottom of the water trough and is provided with a control circuit, the water tank is arranged in the water trough, a drain hole is formed in a bottom of the water tank, a drain control device is arranged at the drain hole, an atomization tube is arranged in the water tank, and a top cover is arranged at a top of the water tank and is provided with a mist outlet matched with the atomization tube.

18. The purification and aroma humidifier according to claim 7, wherein the automatic drip feeder adopts at least one of the following modes to add the aromatic liquid:
   (1) to add the aromatic liquid via a preset control mode of the purification and aroma humidifier;
   (2) to add the aromatic liquid via a manual addition mode on a control panel;
   (3) to control the addition of the aromatic liquid via mobile phone APP software.

19. The purification and aroma humidifier according to claim 13, wherein a bottom cover is arranged at the bottom of the water trough and is provided with a control circuit, the water tank is arranged in the water trough, a drain hole is formed in a bottom of the water tank, a drain control device is arranged at the drain hole, an atomization tube is arranged in the water tank, and a top cover is arranged at a top of the water tank and is provided with a mist outlet matched with the atomization tube.

20. The purification and aroma humidifier according to claim 17, wherein the bottom cover is arranged at the bottom of the water trough and is provided with the control circuit, the water tank is arranged in the water trough, the drain hole is formed in the bottom of the water tank, the drain control device is arranged at the drain hole, the atomization tube is arranged in the water tank, and the top cover is arranged at the top of the water tank and is provided with the mist outlet matched with the atomization tube.

* * * * *

UNITED STATES PATENT AND TRADEMARK OFFICE
CERTIFICATE OF CORRECTION

| | | |
|---|---|---|
| PATENT NO. | : 11,491,253 B2 | Page 1 of 1 |
| APPLICATION NO. | : 16/383939 | |
| DATED | : November 8, 2022 | |
| INVENTOR(S) | : Shifei Meng and Xiaowen Zheng | |

It is certified that error appears in the above-identified patent and that said Letters Patent is hereby corrected as shown below:

On the Title Page

"(73) Assignees: VANSEN INIELLIGENT MANUFACTURING CO., LTD., Fujian (CN); Naturesque LLC, Maple Grove, MN (US)" to -- (73) Assignees: VANSEN INTELLIGENT MANUFACTURING CO., LTD., Fujian (CN) ; Naturesque LLC, Maple Grove, MN (US) --.

And

"(74) Attorney, Agent, or Firm — Iuncy, Geissler, Olds & Lowe, P.C." to -- (74) Attorney, Agent, or Firm — Muncy, Geissler, Olds & Lowe, P.C. --.

Signed and Sealed this
Seventeenth Day of January, 2023

Katherine Kelly Vidal
*Director of the United States Patent and Trademark Office*